United States Patent
Zachmann et al.

(10) Patent No.: US 6,535,615 B1
(45) Date of Patent: Mar. 18, 2003

(54) METHOD AND SYSTEM FOR FACILITATING INTERACTION BETWEEN IMAGE AND NON-IMAGE SECTIONS DISPLAYED ON AN IMAGE REVIEW STATION SUCH AS AN ULTRASOUND IMAGE REVIEW STATION

(75) Inventors: Eric Zachmann, Brighton, MI (US); Paul Schmitter, Dexter, MI (US); David A. Rock, Saline, MI (US); Jeffrey S. Hastings, Los Altos, CA (US)

(73) Assignee: Acuson Corp., Mountain View, CA (US)

( * ) Notice: Subject to any disclaimer, the term of this patent is extended or adjusted under 35 U.S.C. 154(b) by 0 days.

(21) Appl. No.: 09/283,099

(22) Filed: Mar. 31, 1999

(51) Int. Cl.[7] .................................................. G06K 9/00
(52) U.S. Cl. ....................................... 382/100; 600/437
(58) Field of Search ................................ 382/128, 130, 382/131, 132, 133, 129; 345/163, 164, 156, 157; 600/437, 447, 452

(56) References Cited

U.S. PATENT DOCUMENTS 5,687,737 A  *  11/1997  Branham et al. ........... 600/525
5,721,849 A       2/1998  Amro
5,786,818 A       7/1998  Brewer et al.
5,835,088 A      11/1998  Jaaskelainen, Jr.
5,872,567 A       2/1999  Amro
6,078,308 A  *   6/2000  Rosenberg .................. 345/145

* cited by examiner

Primary Examiner—Bhavesh Mehta
Assistant Examiner—Abolfazl Tabatabai

(57) ABSTRACT

A method and system are provided for facilitating interaction between image and non-image sections displayed on an image review station. With the preferred embodiments, a user can interact with image and non-image sections without changing focus between the sections, thereby allowing the user to be much more efficient in the use of the medical image review station. In one presently preferred embodiment, an image review station processor determines which operation should be performed based on a position of a displayed pointer, regardless of which section is under focus. In another presently preferred embodiment, a user interface device is dedicated to either an image or non-image section such that input from the dedicated user interface device will be applied to the corresponding section regardless of which section is in focus. In a third presently preferred embodiment, the processor determines what operation will be performed based on the type of command received by a voice recognition user interface device, regardless of which section is under focus.

25 Claims, 3 Drawing Sheets

METHOD AND SYSTEM FOR FACILITATING INTERACTION BETWEEN IMAGE AND NON-IMAGE SECTIONS DISPLAYED ON AN IMAGE REVIEW STATION SUCH AS AN ULTRASOUND IMAGE REVIEW STATION

BACKGROUND

Current medical image review stations present both an image section and a non-image section (such as an image report and/or a patient worksheet) to a user in a windows-type environment. In this environment, a user must first establish a focus in a window before interacting with the window. Once a window is under focus, commands from user interface devices are sent to the object, application, process, or program running in that window. To provide input into another window, the user must first change focus to the new window, usually by positioning a pointer over the other window and single-clicking a mouse button.

When using an image review station, a user frequently changes focus between image and non-image sections. For example, to enter a diagnosis based on a set of medical images, a user first establishes focus in the report section by positioning a pointer over the non-image section and single-clicking a mouse button. Then, the user positions the cursor in the appropriate field and enters the data. If the user needs to interact with the displayed images to form his diagnosis, he first changes focus to the image section and then manipulates the images. To enter more data into the report, the user re-establishes focus in the report section and enters the additional data. Because a user is frequently switching back and forth between the image and non-image sections during the normal course of interacting with the review station, the windows-type environment, which assumes that a user in focused at doing only one activity at a time, reduces the user's productivity.

There is a need, therefore, to facilitate interaction with image and non-image sections displayed on an image review station to increase user productivity.

SUMMARY

The present invention is defined by the following claims, and nothing in this section should be taken as a limitation on those claims.

By way of introduction, the preferred embodiments described below provide a method and system for facilitating interaction between image and non-image sections displayed on an image review station. With these preferred embodiments, a user can interact with image and non-image sections without changing focus between the sections, thereby allowing the user to be much more efficient in the use of the medical image review station.

In one presently preferred embodiment, an image review station processor determines which operation should be performed based on a position of a displayed pointer, regardless of which section is under focus. In another presently preferred embodiment, a user interface device is dedicated to either an image or non-image section such that input from the dedicated user interface device will be applied to the corresponding section regardless of which section is in focus. In a third presently preferred embodiment, the processor determines what operation will be performed based on the type of command received by a voice recognition user interface device, regardless of which section is under focus.

The preferred embodiments will now be described with reference to the attached drawings.

DETAILED DESCRIPTION OF THE PRESENTLY PREFERRED EMBODIMENTS

Figure 1:
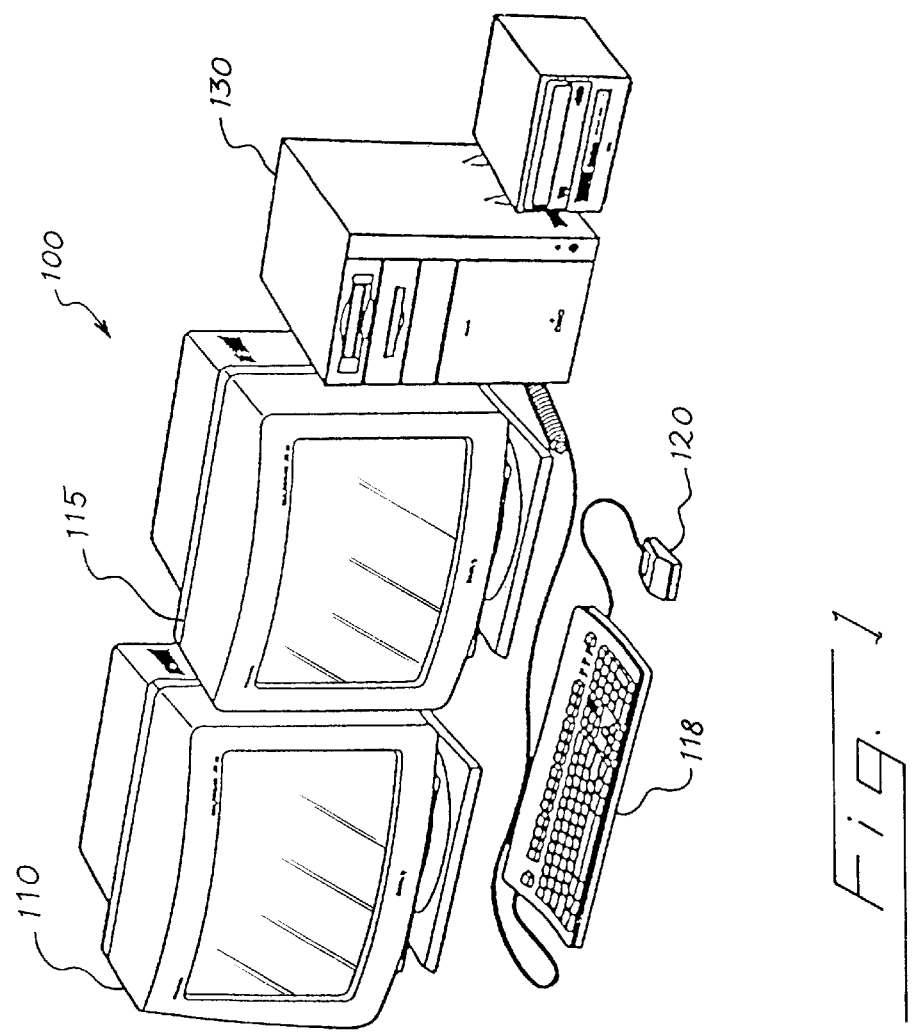
FIG. 1 is an illustration of a medical image review station of a preferred embodiment.

Turning now to the drawings, FIG. 1 is an illustration of a medical image review station 100 of a presently preferred embodiment. The medical image review station 100 comprises a first and second display device 110, 115, a keyboard 118, a mouse 120, and a processor 130 (which comprises analog or digital hardware and/or software components). Although two display devices are shown in FIG. 1, the medical image review station 100 can have only one display device or can have three or more display devices. When multiple display devices are used, the processor 130 can be configured to treat the multiple display devices as if they were a single display device (i.e., each separate display device presents only part of a single display output).

The image review station 100 of FIG. 1 is operative to display medical images. As used herein, the term "medical image" includes, but is not limited to, an ultrasound image as well as an image generated by any of the following modalities: computed radiography, magnetic resonance, angioscopy, color flow Doppler, cystoscopy, diaphanography, echocardiography, fluoresosin angiography, laparoscopy, magnetic resonance angiography, positron emission tomography, single-photon emission computed tomography, x-ray angiography, computed tomography, nuclear medicine, biomagnetic imaging, culposcopy, duplex Doppler, digital microscopy, endoscopy, fundoscopy, laser surface scan, magnetic resonance spectroscopy, radiographic imaging, thermography, and radio fluroscopy.

While FIG. 1 shows a keyboard 118 and a mouse 120, it is important to note that any suitable user interface device can be used. As used herein, the term "user interface device" is intended to broadly refer to any device that allows a user to generate a command to the processor 130 of the image review station 100. In reference to FIG. 2, a user interface device can refer to a single user interface device (such as a mouse 200) or to individual user interface elements of a single user interface device (such as a left button 210, a right button 220, a rotatable and/or depressable scroll wheel 230, and a mouse ball (not shown) that moves when the mouse 200 is moved by a user). As another example, a user interface device can refer to a keyboard 118 or to the individual keys (e.g., such as alphanumeric keys or specialized keys such as page up, page down, and the arrow keys) on the keyboard. While a user interface device (such as a mouse, trackball, and touch pad) can be sensitive to physical manipulation, user interface devices are not limited to devices that a user can physically manipulate. For example, a user interface device can be a voice recognition device that converts a voiced command into an electronic command suitable for use by the image review station processor 130.

Figure 3:
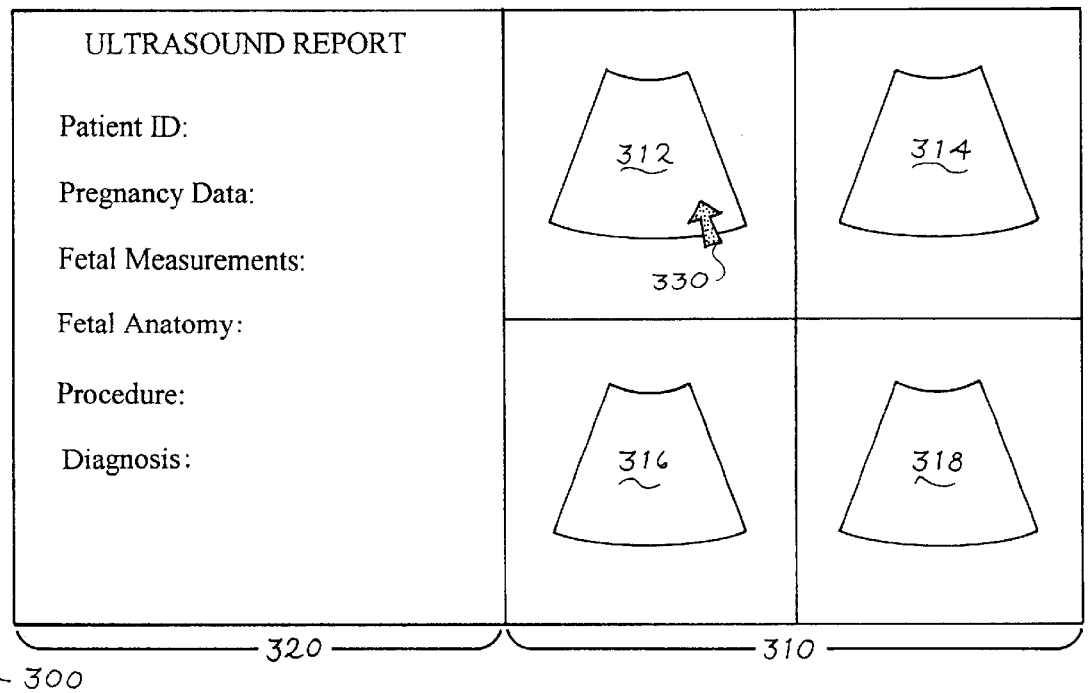
FIG. 3 is an illustration of an output of a monitor of an image review station of a preferred embodiment.

The processor 130 of the image review station 100 is operative to execute one or more applications for medical image review. For example, the processor 130 can execute a single application that displays image and non-image sections 310, 320 to a user on a single monitor 300, as shown in FIG. 3. Alternatively, the image and non-image sections can each be associated with their own program. In FIG. 3, the image section 310 comprises a series of captured ultrasound images 312, 314, 316, 318, and the non-image section 320 comprises an image report section. While FIG. 3 shows a single monitor 300 displaying both an image section 310 and a report section 320, in an alternate embodiment, two monitors are used—one displaying the image section, and the other displaying both a report section and a patient worksheet section.

As used herein, the term "image section" refers to the section of the display that presents medical images, while the term "non-image section" refers to the section of the display that presents textual or other non-image data. The non-image section can comprise a single non-image section or multiple non-image sections (e.g., an image report section, a patient worksheet section, or both an image report and a patient worksheet section). In addition to providing the user with image and non-image information, the image and non-image sections 310, 320 allow the user to provide input to interact with the sections. For example, the user can input information (such as fetal anatomy, procedure, or diagnosis data) into an image report section 320 and can make measurements of imaged structure by manipulating a pointer positioned over a medical image in the image section 310. In the presently preferred embodiment both the image and non-image sections operate within a single application. In an alternate embodiment, the image and non-image sections each operate within their own respective application.

With conventional image review stations, when a focus is established in one of the sections, the application (or portion of the application) that is responsible for that section responds to commands given by any and all of the user interfaces devices of the station. With the image review station 100 of the presently preferred embodiment, the processor 130 facilitates user input into the image and non-image sections 310, 320 without requiring the user to change focus between the image and non-image sections 310, 320. Specifically, the processor 130 is operative to apply at least some of the commands given by at least some of the user interface devices to the image or non-image sections regardless of which section is under focus. In this way, the user can interact with both image and non-image sections without changing focus between the sections.

The following paragraphs describe three preferred implementations that facilitate user input into image and non-image sections without requiring the user to change the focus between the sections.

Context Sensitive Input

In one preferred embodiment, the operation that is performed by the processor 130 in response to a command from a user input device is determined by the position of a pointer 330 in the display 300. As used herein, the term "operation" broadly refers to any action or actions taken by the processor 130 in response to a command from a user interface device. For example, an operation can be simply inserting a character into a field in an image report in response to a letter typed on a keyboard or can be performing a more complicated task, such as making a measurement of a structure shown in an image.

Figure 4:
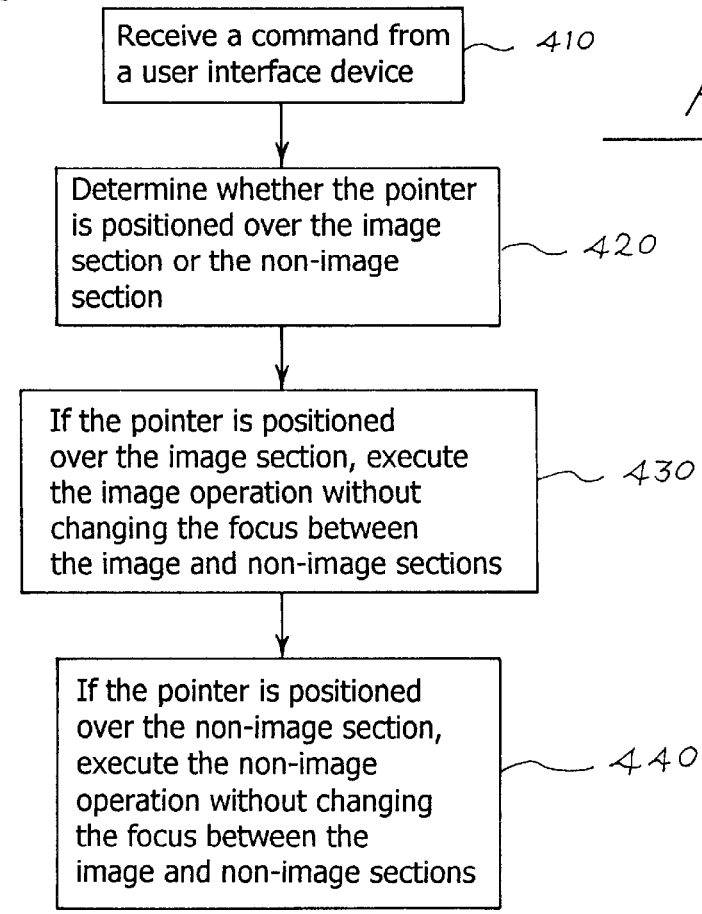
FIG. 4 is a flow chart of a method of a preferred embodiment for determining an operation to be performed based on a position of a pointer in an image review station display.

FIG. 4 is a flow chart of a method illustrating this preferred embodiment. As shown in FIG. 4, the processor 130 first receives a command from a user interface device (step 410). Then, the processor 130 determines whether the pointer 330 is positioned over the image section 310 or the non-image section 320 (step 420). If the pointer 330 is positioned over the image section 310, the image operation is executed without changing the focus between the image and non-image sections (step 430). However, if the pointer 330 is positioned over the non-image section 320, the non-image operation is executed without changing the focus between the image and non-image sections (step 440).

The following examples will illustrate this preferred embodiment. In these examples, a mouse is used to generate three commands: a single-click command, a double-click command, and a single-click-and-drag command. As described below, each of these commands is associated with both an image section operation and a non-image section operation. Which operation will be performed by the processor 130 is determined by which section is indicated by the pointer and not by which section is under focus. It is important to note that the following are merely examples and that other user interface devices and other image and non-image operations associated with a user interface command can be used and that means other than a pointer can be used to select the image and non-image sections 310, 320 without changing focus.

Returning to the examples, when a single-click command is received, the processor 130 determines whether the pointer 330 is positioned over the image section 310 or the non-image section 320. If the pointer 330 is positioned over the image section 310, the processor 130 selects the image that is indicated by the pointer 330. If the pointer 330 is positioned over the non-image section 320, the processor 130 positions a text cursor in the location indicated by the pointer 330. If the pointer 330 is positioned in the image section 310 when a double-click command is received, the processor 130 zooms the image under the pointer 330. If, however, the pointer 330 is positioned in the non-image section 310, the processor 130 highlights the word indicated by the pointer 330. Further, if a single-click-and-drag command is received when the pointer 330 is positioned in the image section 310, a measurement of the image is made along the click-and-drag sweep. On the other hand, if the single-click-and-drag command is received when the pointer 330 is positioned in the non-image section 320, the processor 130 selects the range of text along the click-and-drag sweep.

Dedicated User Interface Device

Figure 5:
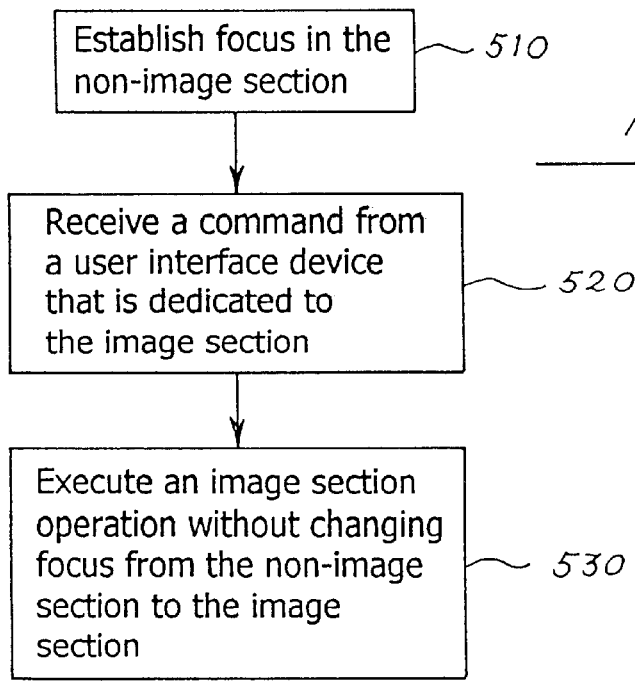
FIG. 5 is a flow chart of a method of a preferred embodiment illustrating the use of a dedicated user interface device associated with either an image or non-image section.

In another preferred embodiment, a user interface device associated with one section (but not the other section) is used to determine what operation will be performed by the processor 130. This preferred embodiment will be described in relation to the flow chart of FIG. 5. First, the processor 130 establishes focus in the non-image section (step 510). Then, the processor 130 receives a command from a user interface device that is dedicated to the image section 310 (step 520). The user interface device is dedicated to the image section 310 in that any command generated by the user interface device is associated with an image section operation and not with a non-image section operation. (In contrast, a single-click command from the mouse in the example described in the preceding section was associated with both an image section and a non-image section operation.) After the processor 130 receives the command from the dedicated user interface device, the processor 130 executes the image section operation without changing focus from the non-image section to the image section (step 530).

The following examples will illustrate this preferred embodiment. In this example, the dedicated user interface device is a scroll wheel of a mouse or one of a set of keys on a keyboard. Each of these dedicated user interface devices is associated only with an image section operation. It is important to note that in an alternative embodiment, the dedicated user interface device is associated only with a non-image section operation, such that selection of the user interface device will execute a non-image section operation even when the focus is in the image section 310. It is also important to note that a dedicated user interface device can take other forms in addition to a scroll wheel 230 or a set of keys on a keyboard.

Figure 2:
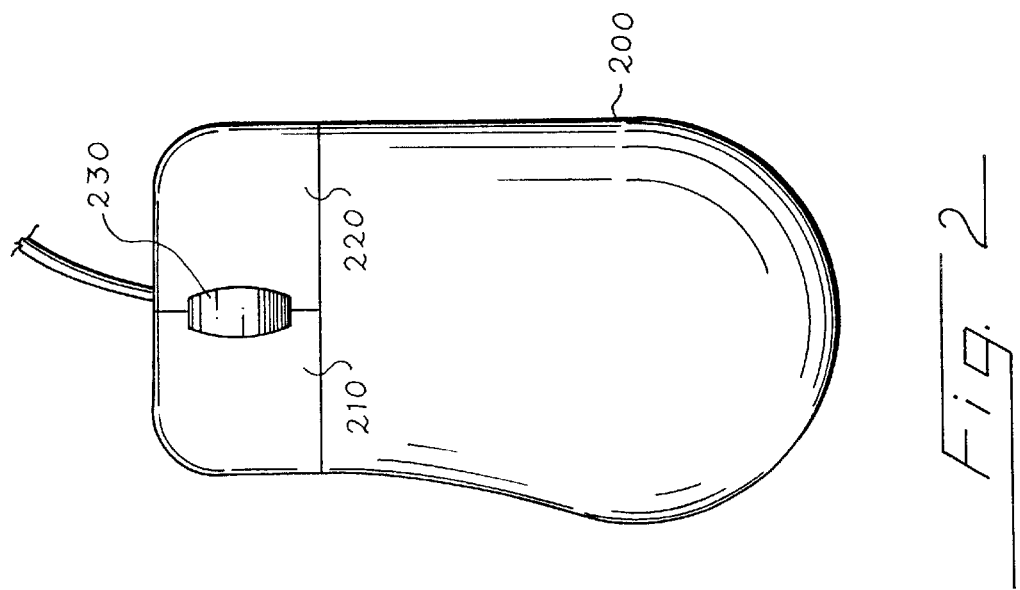
FIG. 2 is an illustration of a mouse with a scroll wheel that can be used with the medical image review station of FIG. 1.

In one example, the dedicated user interface element is a scroll wheel 230 of a mouse 200 (see FIG. 2). The scroll wheel 230 is dedicated to the image section 310 such that even if the focus is in the non-image section 310, manipulation of the scroll wheel 230 will cause an operation to be performed with respect to the image section 310. For example, the processor 130 can be configured so that rotation of the scroll wheel 230 will cause the displayed images to scroll up or down by one or more rows or pages. Appendix I (which describes ScrollWheel events that cause image scrolling regardless of which section 310, 320 is under focus) and U.S. patent application Ser. No. 09/183,862 (which is assigned to the assignee of the present application and is hereby incorporated by reference) provide further details of a preferred implementation of this preferred embodiment.

The processor 130 can also be configured so that when the user depresses the scroll wheel 230 (without rotating the scroll wheel), the current examination is closed (and marked as read) and the next examination is automatically displayed to the user regardless of which section 310, 320 is under focus. The processor 130 can determine which examination is next based on the location of the examination (e.g., in-patient or out-patient), the type of examination, or the time of the examination, for example. The order of examinations can also be programmed by the user or can be automatically determined by the processor 130 based on a predicted priority scheme.

In another example, the dedicated user interface element is a set of keys on a keyboard. As used herein, the term "set of keys" refers to one or more keys on a keyboard. In one presently preferred embodiment, the set of keys includes the function keys (e.g., F1, F2, F3, . . . ), the Page Up/Page Down Keys, the arrow up/arrow down keys, and the Home and End keys, and this set of keys corresponds to image navigation functions. For example, when a user depresses the Page Up key, the images displayed in the image section 310 scroll up by one page even if the focus is in the non-image section 310. Appendix II provides further details of a preferred implementation of this preferred embodiment.

Voice Generated Events

Figure 6:
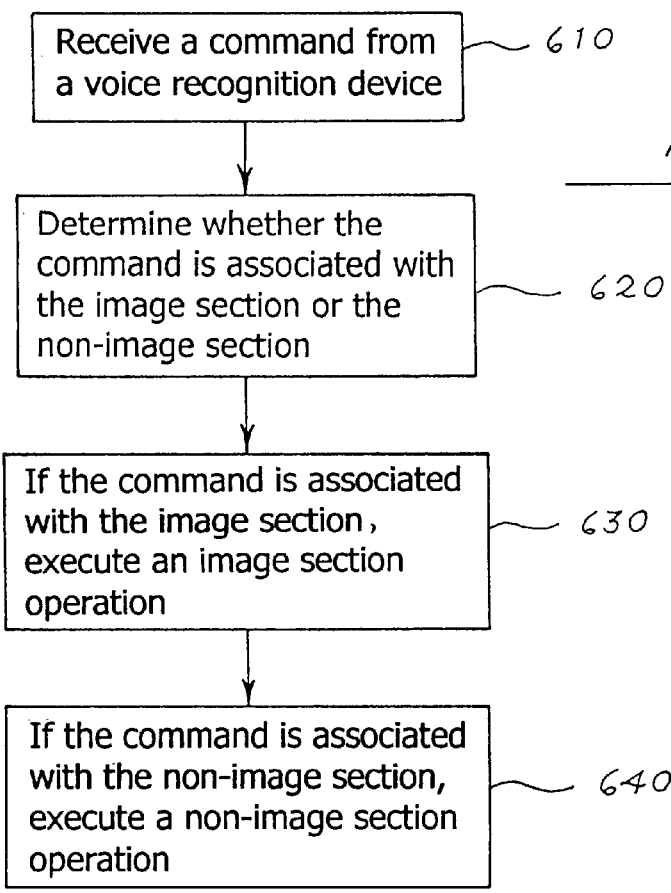
FIG. 6 is a flow chart of method of a preferred embodiment in which a processor determines what operation will be performed based on a type of command received by a voice recognition user interface device.

In another preferred embodiment, the image review station comprises a voice recognition user interface device, as described in U.S. patent application Ser. No. 09/239,271, which is assigned to the assignee of the present application and is hereby incorporated by reference. This preferred embodiment will be illustrated in reference to the flow chart of FIG. 6. First, the processor 130 receives a command from a voice recognition device (step 610). The command is associated with either the image section 310 or the non-image section 320 but not both. The processor 130 then determines whether the command is associated with the image section 310 or the non-image section 320 (step 620). If the command is associated with the image section 310, the processor 130 executes an image section operation without changing a focus between the image and non-image sections 310, 320 (step 630). Alternatively, if the command is associated with the non-image section 320, the processor 130 executes a non-image section operation without changing a focus between the image and non-image sections 310, 320 (step 640).

As an example of this preferred embodiment, consider the situation in which a user voices the command "page up" into a voice recognition user interface device. The processor 130 determines whether the voiced "page up" command is associated with the image or the non-image section 310, 320 by first translating the voice command into an electronic command. In this example, the "page up" command is translated into the same electronic command that is generated by the keyboard when a user depresses the Page Up key. The processor 130 recognizes that the "page up" command is associated with the image section 310 and, without changing focus to the image section, executes an image section operation that scrolls the images up by one page. On the other hand, if the user voiced the command "normal diagnosis," the processor 130 would recognize the command as a macro trigger and insert a textual phrase associated with that macro into the field in the image report of the non-image section 310.

With the above-described preferred embodiments, at least some commands from at least some user interface devices of the image review station will cause an image or non-image operation to be performed without changing focus to the image or non-image section, respectively. By reducing the need to frequently switch back and forth between the image and non-image sections during the normal course of interacting with the review station, these preferred embodiments increase the user's productivity by facilitating interaction between the image and non-image sections. Of course, any user interface command not associated any or all of these three preferred embodiments can be handled in a focus-dependent manner so that focus-dependent and focus-independent user input can occur simultaneously. For example, the alphanumeric keys on a keyboard can be handled in a focus-dependent manner while the Page Up/Page Down keys are handled in a focus-independent manner as described above. In this way, when the focus is established in the report section, a user can type his diagnosis using the alphanumeric keys on the keyboard and scroll the displayed images without changing focus to the image section by depressing the Page Up/Page Down keys.

It is intended that the foregoing detailed description be understood as an illustration of selected forms that the invention can take and not as a definition of the invention. It is only the following claims, including all equivalents, that are intended to define the scope of this invention.

APPENDIX I

ScrollWheelRegions are used to implement synchronized and unsynchronized image scrolling. In this example we have two computer monitors and one lightbox. The Lightbox is created by the application. The ImageAreas contain images and know how to scroll them. The Lightbox creates ImageAreaOne on the first computer monitor and ImageAreaTwo for the second computer monitor. The Lightbox also has a ScrollWheelRegionOne for the first monitor and ScrollWheelRegionTwo for the second monitor. When the ScrollWheelRegions are created the Lightbox passes itself as a ScrollWheelRegionInterface to the ScrollWheelRegions that it creates so that the ScrollWheelRegions can tell the Lightbox when a ScrollWheellEvent has occured.

Though a ScrollWheelRegion is used to scroll images and is therefore associated with a ScrollImageArea the ScrollWheelRegion does not have to be the same size as the ImageArea and is typically bigger so that spinning the scrollwheel outside of the ImageAreas bounds will still cause the ImageAreas to page the Images.

Illustrating Scenario:

Setup: There are two computer monitors. Each computer monitor has images on them.

Goal: The user wants to scroll the images on both monitors up one page by using the scroll wheel on the mouse.

Steps: The user spins the wheel away from himself ScrollWheelRegionOne. The ScrollWheelRegion is a Windows® window so it receives the event. HandleWin32Event is called with the WM_MOUSEWHEELUP event. The ScrollWheelRegion calls the Lightbox via the ScrollWheelRegionInterface call doScrollWheelSpinTowardResponse. If the ScrollLock is set to true then the Lightbox tells ImageAreaOne and ImageAreaTwo to scrollImagesUpOnePage and both ImageAreas show the previous page of images. If the ScrollLock is not set then the Lightbox only calls the ImageArea that it associates with the particular ScrollWheelRegion that received the ScrollWheelEvent. In this example ScrollWheelRegionOne corresponds to ImageAreaOne and the images in ImageAreaOne are paged up to a previous page and the images on ImageAreaTwo are not scrolled.

```
Pseudo Code
class ScrollWheelRegion
{
        ScrollWheelRegion( LocationOfScrollWheelRegion,
                SizeOfScrollWheelRegion,
                inScrollWheelRegionInterface );
        HandleWin32Event( inWin32Event )
        {
                if( inWin32Event == WM_MOUSEWHEELUP )
                {
        inScrollWheelRegionInterface.doScrollWheelSpinTowardResponse( this );
                }
                // . . .
        }
}
class Lightbox
  : public ScrollWheelRegionInterface
{
        // inherited methods
        do ScrollWheelSpinTowardResponse( inScrollWheelRegion )
        {
                // the scroll wheel was rotated toward the user
                // therefore show previous page
                // if scroll lock is set that means synchronize the
                // scrolling between the image areas
                if ( scrollLock )
                {
                        ImageAreaOne.scrollImagesUpOnePage()
                        ImageAreaTwo.scrollUpPage()
                }
                else
                {
                        if ( mScrollWheelRegionOne ==
                            inScrollWheelRegion )
                        {
                                mImageAreaOne.scrollImagesUpOnePage()
                        }
                        else
                        {
                                mImageAreaTwo.scrollImagesUpOnePage()
                        }
                }
        }
        doScrollWheelSpinAwayResponse( inScrollWheelRegion )
        {
                // . . .
        }
        // member variables
        ScrollWheelRegion mScrollWheelRegionOne;
        ImageArea mImageAreaOne;
        ScrollWheelRegion mScollWheelRegionTwo;
        ImageArea mImageAreaTwo;
}
```

APPENDIX II

KeystrokeBehaviorInterfaces are used to implement synchronized and unsynchronized image scrolling. In this example we have two computer monitors and one lightbox. The Lightbox is created by the application. The ImageAreas contain images and know how to scroll them. The Lightbox creates ImageAreaOne on the first computer monitor and ImageAreaTwo for the second computer monitor. The Lightbox passes itself as a KeystrokeBehaviorInterface when it registers with the keyboard to receive pageUp and pageDown messages.

Illustrating Scenario:

Setup: There are two computer monitors. Each computer monitor has images on them.

Goal: The user wants to scroll the images on the second monitor up one page by pressing the Alt-PageUp key.

Steps: The user presses the Alt-PageUp key. The Keyboard is registered with Windows® to receive the Keyboard events. In the Keyboard class the HandleWin32Event method is called with the WM_PAGEUPKEY event. The Keyboard calls the Lightbox via the KeystrokeBehaviorInterface call doPageUpKeyPressedResponse. If the ScrollLock is set to true then the Lightbox tells ImageAreaOne and ImageAreaTwo to scrollImagesUpOnePage and both ImageAreas show the previous page of images. If the ScrollLock is not set then the Lightbox checks to see if the Alt key was pressed with the PageUpKey. In this example it was so that means to scroll the images on the second monitor by telling ImageAreaTwo to pageUp its images.

```
Pseudo Code
class KeystrokeBehaviorInterface
{
doPageUpKeyPressedResponse( inKeyModfier )
doPageDownKeyPressedResponse( inKeyModifier )
}
class Keyboard
{
        register( inKeystrokeBehaviorInterface )
        HandleWin32Event( inWin32Event )
        {
                if( inWin32Event == WM_PAGEUPKEY )
```

-continued

```
        {
                inKeystrokeBehaviorInterface.
                        doPageUpKeyPressedResponse(
                inWin32Event.keyModifiers );

// . . .
        }
}
class Lightbox
    : public KeystrokeBehaviorInterface
{
        Lightbox
        {
                // Lightbox registers self with the Keyboard as a
KeystrokeBehaviorInterface
                Keyboard.register( this );
                create ImageAreaOne
                create ImageAreaTwo;
        }
        // inherited methods
        doPageUpKeyPressedResponse( inKeyModifier )
        {
                // the page up key was pressed by the user
                // therefore show previous page
                // if scroll lock is set that means synchronize the scrolling
                // between the image areas
                if( scrollLock )
                {
                        ImageAreaOne.scrollImagesUpOnePage()
                        ImageAreaTwo.scrollUpPage()
                }
                else
                {
                        if( Alt=!= inKeyModifier )
                        {
                                mImageAreaTwo.scrollImagesUpOnePage()
                        }
                        else
                        {
                                mImageAreaOne.scrollImagesUpOnePage()
                        }
                }
        }
        doPageDownKeyPressedResponse()
        {
                // . . .
        }
        // member variables
        ImageArea mImageAreaOne;
        ImageArea mImageAreaTwo;
}
```

What is claimed is:

1. In a medical image review station displaying an image section, a non-image section, and a pointer positioned over the image or non-image section, wherein one of the image section and the non-image section is under focus and the other is not under focus, a method for executing a command from a user interface device without changing a focus between the image and non-image sections, the method comprising:

(a) receiving a command from a user interface device;

(b) determining whether a pointer is positioned over an image section or a non-image section;

(c) without changing focus between the image and non-image sections, executing an image section operation associated with the command in response to the pointer being positioned over the image section; and (d) without changing the focus between the image and non-image sections, executing a non-image section operation associated with the command in response to the pointer being positioned over the non-image section.

2. The method of claim 1, wherein (a) comprises receiving a single-click command from a mouse and wherein (c) comprises selecting an image indicated by the pointer.

3. The method of claim 1, wherein (a) comprises receiving a single-click command from a mouse and wherein (d) comprises positioning a text cursor in a location indicated by the pointer.

4. The method of claim 1, wherein (a) comprises receiving a double-click command from a mouse and wherein (c) comprises enlarging an image indicated by the pointer.

5. The method of claim 1, wherein (a) comprises receiving a double-click command from a mouse and wherein (d) comprises selecting a word indicated by the pointer.

6. The method of claim 1, wherein (a) comprises receiving a single-click-and-drag command from a mouse herein (c) comprises making a measurement of an image along a click-and-drag sweep.

7. The method of claim 1, wherein (a) comprises receiving a single-click-and-drag command from a mouse and wherein (d) comprises selecting a range of text along a click-and-drag sweep.

8. In a medical image review station displaying an image section and a non-image section, a method for executing a command from a user interface device without changing a focus between the image and non-image sections, the method comprising:

(a) establishing a focus in a non-image section;

(b) receiving a command from a user interface device associated with an image section and not associated with the non-image section, said command being associated with an image section operation and not being associated with a non-image section operation; and (c) without changing a focus from the non-image section to the image section, executing the image section operation.

9. The method of claim 8, wherein (b) comprises receiving a command from a scroll wheel of a mouse, and wherein (c) comprises executing an image scrolling operation.

10. The method of claim 8, wherein (b) comprises receiving a command from a scroll wheel of a mouse, and wherein (c) comprises closing a current examination and automatically displaying a next examination.

11. The method of claim 10 further comprising determining a next examination from a set of examinations based on examination location.

12. The method of claim 10 further comprising determining a next examination from a set of examinations based on user preference.

13. The method of claim 10 further comprising determining a next examination from a set of examinations based on a predicted priority scheme.

14. The method of claim 8, wherein (b) comprises receiving a command from a keyboard, and wherein (c) comprises executing an image scrolling operation.

15. The method of claim 8, wherein when focus is established in the non-image section in (a), the image section is not under focus.

16. In a medical image review station displaying an image section and a non-image section, a method for executing a command from a user interface device without changing a focus between the image and non-image sections, the method comprising:

(a) establishing a focus in an image section;

(b) receiving a command from a user interface device associated with a non-image section and not associated with the image section, said command being associated with a non-image section operation and not being associated with an image section operation; and (c) without changing a focus from the image section to the non-image section, executing the non-image section operation.

17. The method of claim 16, wherein when focus is established in the image section in (a), the non-image section is not under focus.

18. In a medical image review station displaying an image section and a non-image section, a method for executing a command from a user interface element without changing a focus between the image and non-image sections, the method comprising:

(a) receiving a command from a voice recognition device, said command being associated with either an image section operation or a non-image section operation but not both;

(b) determining whether the command is associated with an image section operation or a non-image section operation;

(c) without changing a focus between the image and non-image sections, executing the image section operation in response to the command being associated with the image section; and (d) without changing a focus between the image and non-image sections, executing the non-image section operation in response to the command being associated with the non-image section.

19. The method of claim 18, wherein (c) comprises executing an image scrolling operation.

20. The method of claim 18, wherein (d) comprises inserting a textual phrase into a field in an image report of the non-image section.

21. The method of claim 18, wherein one of the image section and the non-image section is under focus and the other is not under focus.

22. A medical image review station comprising:

at least one monitor;

at least one user interface device; and a processor coupled with said at least one monitor and said at least one user interface device, the processor being operative to display an image and a non-image section on said at least one monitor, wherein one of the image section and the non-image section is under focus and the other is not under focus; the processor being further operative to execute an operation associated with a command received from said at least one user interface device regardless of which section is under focus.

23. The medical image review station of claim 22, wherein said at least one user interface device comprises a mouse.

24. The medical image review station of claim 22, wherein said at least one user interface device comprises a keyboard.

25. The medical image review station of claim 22, wherein said at least one user interface device comprises a voice recognition user interface device.

* * * * *